(12) United States Patent
White et al.

(10) Patent No.: US 8,323,249 B2
(45) Date of Patent: Dec. 4, 2012

(54) INTEGRATED VASCULAR DELIVERY SYSTEM

(75) Inventors: Steven B. White, Ann Arbor, MI (US); Adrienne Harris, Clinton, MI (US); Merrell Sami, Arlington, VA (US); Elyse Kemmerer, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 109 days.

(21) Appl. No.: 12/855,013

(22) Filed: Aug. 12, 2010

(65) Prior Publication Data

US 2011/0040281 A1 Feb. 17, 2011

Related U.S. Application Data

(60) Provisional application No. 61/233,859, filed on Aug. 14, 2009.

(51) Int. Cl.
*A61M 31/00* (2006.01)
*A61M 5/00* (2006.01)

(52) U.S. Cl. ........ 604/177; 604/513

(58) Field of Classification Search ......... 604/174, 604/177, 179, 180, 513
See application file for complete search history.

(56) References Cited

U.S. PATENT DOCUMENTS

| | | | |
|---|---|---|---|
| 4,380,234 A * | 4/1983 | Kamen | 604/180 |
| 5,375,589 A | 12/1994 | Bhatta | |
| 5,643,216 A * | 7/1997 | White | 604/174 |
| 6,805,860 B1 | 10/2004 | Alt | |
| 7,799,000 B2 * | 9/2010 | Silich | 604/174 |
| 7,918,828 B2 * | 4/2011 | Lundgaard et al. | 604/174 |
| 2006/0094983 A1 | 5/2006 | Burbank et al. | |
| 2008/0195033 A1 | 8/2008 | Eagleson et al. | |

* cited by examiner

*Primary Examiner* — Kevin C Sirmons
*Assistant Examiner* — Bradley Osinski
(74) *Attorney, Agent, or Firm* — Harness, Dickey & Pierce, P.L.C.

(57) ABSTRACT

An integrated vascular delivery system having a frame configured to receive a catheter insertable in a patient to deliver fluid at an insertion site. The frame includes a first hub, a second hub, and a pair of flexible lateral members extending between the hubs and including a tubular lateral member. The system also includes a fluidic channel that fluidically communicates with the catheter, wherein the fluidic channel passes through the tubular lateral member and at least one of the hubs, and includes a fixed turnabout portion in which fluid flows in a direction different from that within the catheter. The first and second hubs provide anchoring points on the patient distributed around the insertion site and on opposite ends of the catheter, thereby anchoring the frame to the patient and stabilizing the catheter. A method is provided for using an integrated vascular delivery system.

25 Claims, 7 Drawing Sheets

INTEGRATED VASCULAR DELIVERY SYSTEM

CROSS-REFERENCE TO RELATED APPLICATIONS

This application claims the benefit of U.S. Provisional Application No. 61/233,859 filed on Aug. 14, 2009, which is incorporated in its entirety by this reference.

FIELD

The present disclosure relates generally to the medical care field, and more specifically to an improved vascular delivery system in the intravenous therapy field.

BACKGROUND

This section provides background information related to the present disclosure which is not necessarily prior art.

Patients undergoing medical treatment often require a form of intravenous (IV) therapy, in which a fluid is administered to the patient through a vein of the patient. IV therapy is among the fastest ways to deliver fluids and medications into the body of the patient. Intravenously infused fluids, which typically include saline, drugs, blood, and antibiotics, are conventionally introduced to the patient through a flexible catheter positioned at any of several venous routes, such as peripheral veins and central veins.

To set up IV therapy with conventional devices and methods, the caregiver positions the catheter over the selected vein and uses a needle within the catheter to pierce the skin and allow insertion of the catheter into the vein. The catheter is typically positioned such that the distal inserted end of the catheter points toward the midline of the patient (e.g., for a peripheral IV line on the arm, the catheter body is positioned on the forearm and points toward the elbow). The caregiver then withdraws the needle from the catheter, leaving the catheter inserted in the vein. The proximal end of the catheter, relative to the midline of the catheter, is fixed to the end of a catheter hub that is proximal relative to the midline of the patient. The caregiver connects the catheter to a fluid supply through external tubing, including extension tubing that is typically attached to the distal end of the catheter hub relative to the midline of the patient, and that the caregiver typically bends into a U-shape. To avoid unscheduled IV line restarts, the catheter and tubing are typically secured against the skin of the patient with tape or similar catheter stabilization devices (CSDs) such as adhesive stabilizing pads that restrain the catheter body.

However, conventional devices and methods for IV therapy have drawbacks. The extension tubing may catch on nearby obstacles during patient movement or caregiver manipulation, which may cause painful vein irritation and compromise the IV. Tape and other existing CSDs are not optimal for stabilization because securing the round, rigid, and bulky components such as the catheter and tubing against the skin can be difficult and ineffective. Tape and other existing CSDs do not fully prevent the catheter from moving within the vein, which leads to patient-endangering complications including catheter dislodgement, infiltration (fluid entering surrounding tissue instead of the vein), and phlebitis (inflammation of the vein). Adhesive stabilizing pads tend to result in other undesired effects, such as skin irritation and/or breakdown due to prolonged concentrated adhesion to the skin. Furthermore, tape and current CSDs restrain the catheter on only one side of the catheter insertion site, and do not prevent the catheter from painfully and dangerously pivoting around the insertion site and moving within the vein.

Thus, there is a need in the intravenous therapy field to create an improved vascular delivery system that overcomes one or more of the drawbacks of the conventional vascular delivery systems. This invention provides such an improved vascular delivery system.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

The following description of preferred embodiments of the present teachings is not intended to limit the disclosure to these preferred embodiments, but rather to enable any person skilled in the art to make and use this invention.

1. Integrated Vascular Delivery System

Figure 1:
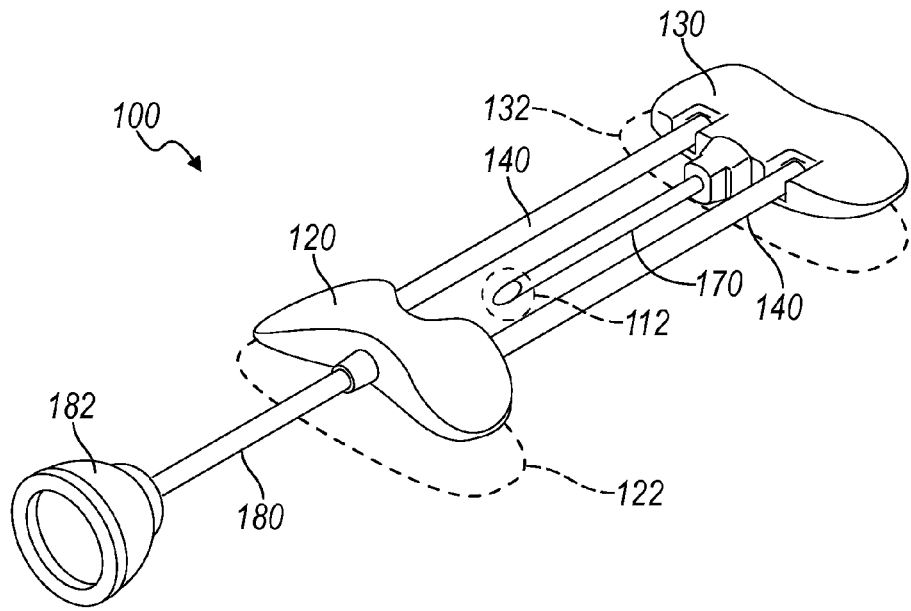
FIG. 1 is the integrated vascular delivery system of a preferred embodiment.
Figure 2:
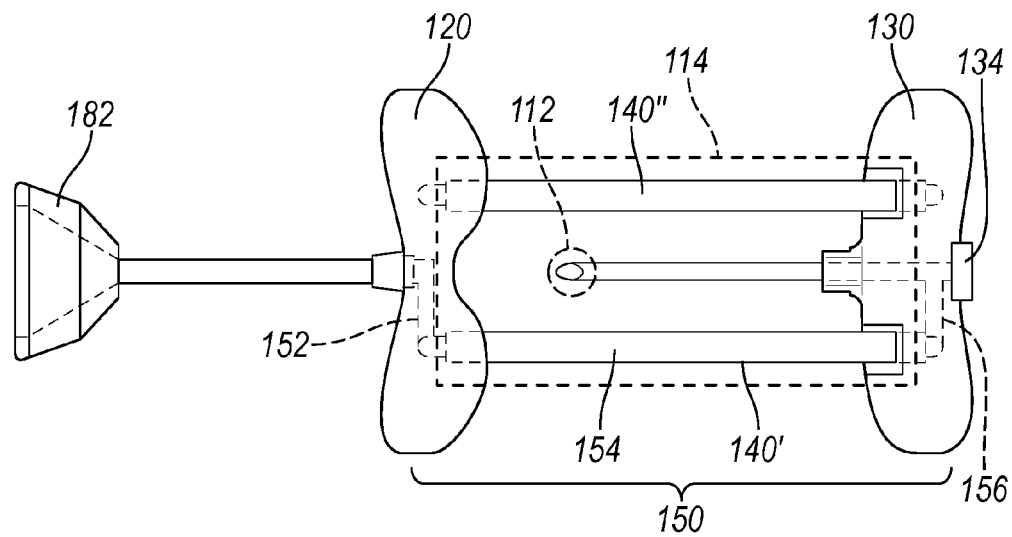
FIG. 2 is a semi-transparent overhead view of the integrated vascular delivery system of a preferred embodiment.

As shown in FIGS. 1 and 2, the integrated vascular delivery system 100 of the preferred embodiments includes: a frame 110 configured to receive a catheter 170 insertable in a patient to deliver fluid at an insertion site, in which the frame includes a first hub 120, a second hub 130, and a pair of flexible lateral members 140 extending between the hubs and including a tubular lateral member 140'; and a fluidic channel 150 that fluidically communicates with the catheter, wherein the fluidic channel 150 passes through the tubular lateral member 140' and at least one of the hubs, and includes a fixed turnabout portion 156 in which fluid flows in a direction different from that within the catheter 170. The first and second hubs preferably provide first and second anchoring points 122 and 132, respectively, on the patient such that the anchoring points are distributed around the insertion site 112 and on opposite ends of the catheter, thereby anchoring the frame to the patient and stabilizing the catheter 170. Fluid flow in the turnabout portion 156 of the fluidic channel 150 is preferably opposite of that within the catheter, and the turnabout portion is preferably fixed in such a way as to reduce the likelihood of snagging or catching on nearby objects. In one preferred embodiment, the system includes a second tubular lateral member 140' and a second fluidic channel 150 that fluidically communicates with the catheter 170 and passes through the second tubular lateral member 140'. In a preferred embodiment, the frame 110 is configured to receive the catheter as an integral part of the system, in which the catheter 170 is embedded in a portion of the frame, and more preferably in one of the hubs. However, in an alternative embodiment the frame 110 is configured to receive a separate catheter, which may snap fit into the frame.

In some versions of the system, the system further includes at least one extension tube 180 and/or a fluid supply adapter 182 that delivers fluid from a fluid supply to the fluidic channel. The system functions to enable access to the vein of a patient undergoing intravenous (IV) therapy with an included catheter, administer fluids intravenously through the catheter, and securely and safely stabilize the catheter on the patient. The system is preferably used to administer drugs, antibiotics, saline, or blood, but may be used to administer any suitable fluid to a patient. The system is preferably used to create, stabilize, and maintain an IV line on a peripheral vein such as on the arm, hand, or leg, but may alternatively be used for central or peripheral venous access on the neck, chest, or abdomen, or any suitable intravenous intraarterial location. The system may further be used to create, stabilize, and maintain any suitable catheter-based access to a patient, such as for the transfer of cerebrospinal fluid.

In a preferred embodiment, the catheter 170, frame 110, fluidic channel 150, extension tubing 180, and/or fluid supply adapter 182 are pre-assembled during manufacture of the system to provide an integrated system that is cost-efficient, reduces IV setup time, and packaging waste. The system preferably stabilizes the catheter 170 on the patient with anchoring points distributed around the insertion site 112, more preferably on at least two opposing sides of the insertion site 112, which may reduce or eliminate painful and dangerous pivoting motions of the catheter 170 that may occur during normal patient movement and/or caregiver manipulations. The system is preferably streamlined by aligning the catheter with the fluid supply adapter and reducing external free tubing, which reduces the likelihood of the system catching or snagging on nearby obstacles. The system is preferably a closed system that reduces possible points of contamination and fluid leakage, which improves safety for both the patient and the caregiver. The system is preferably compatible with existing conventional catheter insertion and IV setup procedures, which enables a caregiver to easily use the system without significant additional training.

The frame 110 of the integrated vascular delivery system functions to stabilize the system on the patient. As shown in FIGS. 1 and 2, the frame 110 preferably includes a first hub 120 on one end of the frame that provides a first anchoring point 122 on the patient, a second hub 130 on an end of the frame approximately opposite to the first hub that provides a second anchoring point 132 on the patient, and two flexible lateral members 140 that extend between and flexibly connect the first hub and the second hub, such that the first hub and the second hub move relative to one another with a significant number of degrees of freedom. In particular, the lateral members 140 preferably are reversibly bendable to fold one of the first and second hubs over the other hub. As shown in FIG. 2, in a preferred embodiment, the lateral members are substantially parallel such that the frame 110 forms an approximately rectangular perimeter 114 around the catheter 170 and insertion site 112. In variations of the frame 110, the frame may include any suitable number of hubs and any suitable number of lateral members, such that the frame forms a perimeter 114 of any suitable shape and size around the insertion site 112. The frame 110 preferably allows visualization of the insertion site 112 of the catheter, such as by leaving an open uncovered area around the catheter, although alternatively the system may include a cover that is transparent, translucent, opaque, or any suitable kind of material, that extends over the frame to cover the insertion site 112 and/or catheter 170. As shown in FIG. 5E, the frame is preferably secured to the patient by securing the first hub 120 and second hub 130 to the patient at the first and second anchoring points, respectively, on opposite sides of the insertion site 112 (preferably distal and proximal to the insertion site) and opposite ends of the catheter 170, thereby stabilizing the catheter. However, the frame 110 may additionally and/or alternatively be secured by securing only the first hub, only the second hub, the lateral members and/or or any other suitable portion of the frame. The frame may alternatively stabilize the catheter at anchoring points located at any suitable locations relative to the catheter insertion site 112. The frame 110, when secured to the patient, enables the integrated vascular system to stabilize the catheter more effectively than conventional catheter securement devices that stabilize the catheter on only one side of the insertion site 112, because stabilizing the catheter on two opposite sides of the insertion site reduces pivoting motions of the catheter that may occur during normal patient movement and/or caregiver manipulations.

The first hub 120 of the frame 110 functions to provide a first anchoring point 122 for the frame. As shown in FIG. 2, in a preferred embodiment, the first hub 120 further functions to house a portion of the fluidic channel 150 within the first hub. The first hub 120 is preferably located on the proximal end of the frame relative to the midline of the patient, such that the first hub provides a first anchoring point 122 proximal to the catheter insertion site relative to the midline of the patient. Alternatively, the first hub 120 may be located on any suitable part of the frame relative to the insertion site 112 to provide a first anchoring point 122 at any suitable location relative to the insertion site 112. As shown in FIG. 5E, the first hub 120 is preferably secured to the skin of the patient with tape, but may additionally and/or alternatively be secured with an adhesive located on the underside of the first hub 120; elastic straps; straps fastened with fasteners such as hooks, hook and loop, or magnets; or any suitable securement mechanism. The first hub may alternatively not be secured to the skin of the patient. In one specific embodiment, the first hub preferably has a relatively wide and thin profile, with a width of approximately 20-30 mm and a thickness of approximately 5 mm. However, the first hub may alternatively be any suitable shape and size. A large width is advantageous for distributing forces over a greater area on the skin, which decreases the chances of the patient developing skin irritations, sores, and other degradations. The thin profile, which is approximately half as thick as conventional vascular access devices, decreases the risk of the hub catching or snagging on bed equipment or other nearby obstacles that could cause the catheter to move within the vein and cause complications such as catheter dislodgement, infiltration, and phlebitis. As shown in FIG. 1, the first hub 120 preferably has rounded edges and preferably has an upper surface that is slightly arched along its lateral axis. The arched upper surface may adapt the first hub to receive tape along the arch for securement to the patient. The first hub may additionally have features that conform to the body of the patient, such as an underside concavity to conform to a limb, finger, or knuckle.

The first hub 120 is preferably made of a rigid or semi-rigid material, such as nylon or silicone, to provide structural support to the frame 110 for stabilizing the system. However, the first hub may alternatively be made of any polymer, metal, composite, or other suitable material. The first hub may be transparent or semi-transparent to allow visualization of the fluid channel 150. The first hub is preferably manufactured through injection molding, but may alternatively be manufactured through stereolithography, casting, milling, or any other suitable manufacturing process known to one skilled in the art.

The first hub 120 and/or the second hub 130 may include a sensor 116 that measures a biometric parameter such as temperature, blood pressure, or pulse rate of the patient. The sensor 116 may additionally and/or alternatively sense any suitable parameter such one pertaining to the fluid, such as pH or flow rate.

The portion of the fluidic channel 150 fixed to the first hub 120 may be coupled to an extension tube and/or fluid supply adapter that function to deliver fluid from a fluid supply to the fluidic channel 150 of the system. The fluid supply adapter preferably includes a connector that attaches the extension tube to a fluid supply, which is preferably a pole-mounted IV bag that supplies fluid through tubing, but may alternatively be a syringe, pump, or other suitable fluid supply. As shown in FIG. 4, the connector is preferably a standard female luer lock connector or Y-connector that commonly interfaces with conventional IV bags, as known to one skilled in the art. Alternatively, the connector may be any suitable male or female connector that is adapted to interface with a fluid supply. The extension tube further functions to provide stress relief if the system is jostled and is preferably made of flexible tubing, such as polymer tubing, but may be a passageway made of any other suitable material. Flexible tubing is advantageous for relieving mechanical stress and reducing chances of patient injury if the system is suddenly disturbed, such as during patient movement or caregiver manipulations. The extension tube is preferably long enough to provide stress relief if needed, but short enough to reduce the chances of the extension tube catching or snagging on nearby obstacles. The length of the extension tube may alternatively be any suitable length, and may depend on the specific application of the system. Other dimensions of the fluid passageway, such as outer diameter and inner diameter, may depend on the specific application of the system.

In alternative versions of the system, the system may include more than one extension tube and/or connector, to facilitate delivering fluid from multiple fluid supplies simultaneously to the system. For example, in an embodiment of the system that includes two fluidic channels 150, the system may include a first extension tube that delivers a first fluid to a first fluidic fluidic channel, and a second extension tube that delivers a second fluid to the second fluidic channel. However, two extension tubes may be useful in applications involving the administering of two separate fluids through the same fluidic channel and catheter.

The second hub 130 of the system is preferably similar to the first hub 120, except as noted below. The second hub 130 functions to provide a second anchoring point 132 for the frame 110, preferably on a distal end of the frame relative to the midline of the patient. The second hub is preferably secured distal to the catheter insertion site 112 relative to the midline of the patient, and in one specific embodiment, approximately 15 mm or less distal to the insertion site. However, the second hub may alternatively be secured in any suitable location relative to the insertion site 112. As shown in FIG. 2, the second hub 130 preferably includes a self-sealing septum 134. The self-sealing septum of the second hub functions to provide an opening for an insertion needle to be inserted into the catheter 170 prior to catheter insertion, and to seal the internal channel second hub after withdrawal of the insertion needle within the catheter after catheter insertion, to prevent escape or leakage of blood and other potential biohazards or other fluids. As shown in FIG. 2, the septum 134 is preferably located on the distal side of the second hub 130 relative to the midline of the patient, and is approximately concentric with the catheter 170. The septum is preferably made of a flexible material that self-seals to form a hermetic seal. This self-sealing septum prevents fluid from passing through the distal side of the second hub relative to the midline of the patient, contributing to a closed system in which blood and other fluids will not exit the integrated vascular delivery device after the needle punctures the patient. The septum 134 may alternatively be sealed with a plug, such as a stopper or sealant material applied to the septum.

The second hub 130 may additionally include a reservoir between the septum 134 and the catheter 170. This reservoir may serve as a flash chamber to contain any blood leakage during withdrawal of the insertion needle from the catheter after catheter insertion, or may serve any other suitable purpose.

The second hub 130 may additionally include features at the connection between the second hub 130 and the lateral members that reduce creasing, collapsing, fracture, or other damage in the lateral members when the lateral members are folded to pass one of the hubs over the other hub during insertion of the catheter into the patient. As an example, the second hub may include rounded edges that are contoured to the natural bend radius of the lateral members, to prevent the lateral members from bending too sharply or bending against a sharp edge. As another example, the second hub may include relief cutouts and/or other reinforcements that encourage the lateral members to bend to their natural bend radius.

The lateral members 140 of the frame 110 function to provide structural stability to the frame by stabilizing the first hub 120 relative to the second hub 130. As shown in FIGS. 1 and 2, the frame 110 preferably includes two flexible lateral members, including at least one tubular lateral member 140'. However, in alternative versions of the frame, the frame may include fewer or more lateral members. The lateral members preferably provide structural stability to the frame, and the tubular lateral member 140' or members preferably house a portion of the fluidic channel 150. The lateral members are preferably parallel with one another and preferably extend between the first and second hubs, to form a perimeter 114 around the catheter 170. However, the lateral members may be in any crossed, non-parallel or any suitable orientation. The lateral members preferably allow the first hub and the second hub to move relative to one another with a significant number of degrees of freedom, including displacement in the compression direction (and subsequent displacement in the tension direction) along the axis of the catheter, displacement in both directions along the other two axes, twisting in both directions along the axis of the catheter, and bending in both directions along the other two axes. In particular, the lateral members are preferably reversibly bendable to fold one of the first and second hubs over the other hub. As shown in FIGS. 5B and 6, during insertion of the catheter into the patient, the lateral members are preferably folded to fold the first hub 120 over the second hub 130, which opens the perimeter 114 around the catheter and exposes the penetrating distal tip of the catheter. The length of the lateral members is preferably approximately 30%-50% longer than the catheter, but may alternatively be shorter or longer depending on the specific application. At least one lateral member 140 may include markings, such as markings similar to those on a ruler, to indicate the depth to which the catheter is inserted into the patient. The lateral members are preferably made of an extruded flexible polymer cut to length and molded to one or both hubs, but may alternatively be made through any suitable manufacturing process and/or out of any suitable material.

In a first preferred embodiment, the pair of lateral members includes a tubular lateral member 140' and a solid lateral member 140". The tubular lateral member is preferably a generally straight, soft, and flexible hollow channel such as medical tubing, but may alternatively be any suitable structure with an internal fluid passageway that houses a portion of the fluidic channel 150. The tubular lateral member is preferably rigid enough to provide structural support to the frame 110, but flexible enough to bend and fold across its length without damage during insertion of the catheter. The tubular lateral member may include additional features that enhance the ability to bend without damage. As an example, the tubular lateral member may be tapered along its length and include a thicker wall and/or larger outer diameter near the bending stress point at the second hub 130. As another example, the tubular lateral member may have an elliptical cross-section that is more resistant to bending damage. As another example, at least a portion of the first lateral member may include extendable and foldable pleats, similar to an accordion, that allow curvature of the lateral member with less bending stress.

As shown in FIG. 2, in the first preferred embodiment, the solid lateral member is preferably similar in shape, and size to the first lateral member so that the frame 110 is structurally symmetrical, but preferably is a "dummy" structure in that it does not house a portion of the fluidic channel 150. The solid lateral member 140" preferably is approximately identical in flexibility and strength as the tubular lateral member 140'. However, the solid lateral member 140" may alternatively have a different shape (e.g., larger diameter or larger thickness) to further enhance stabilization of the first hub 120 relative to the second hub. Similar to the tubular lateral member 140', the solid lateral member 140" may additionally include features that enhance the ability to bend without damage.

Figure 3:
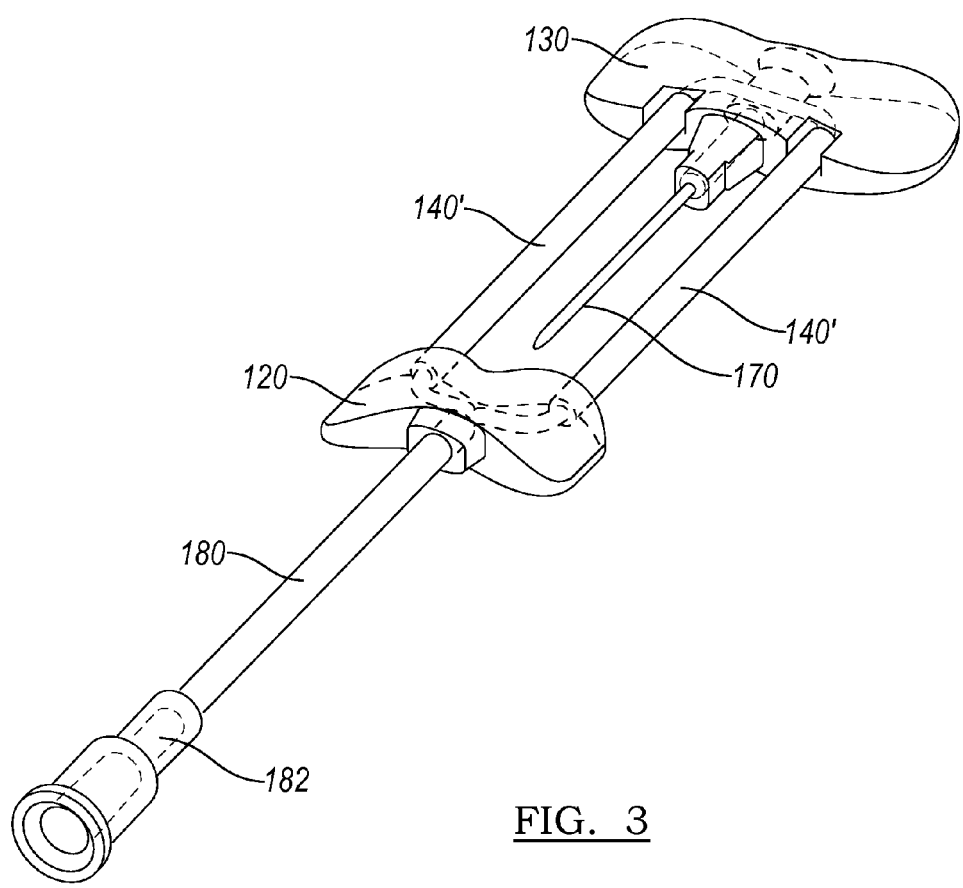
FIG. 3 is a semi-transparent view of the integrated vascular delivery system of another preferred embodiment.
Figure 4A:
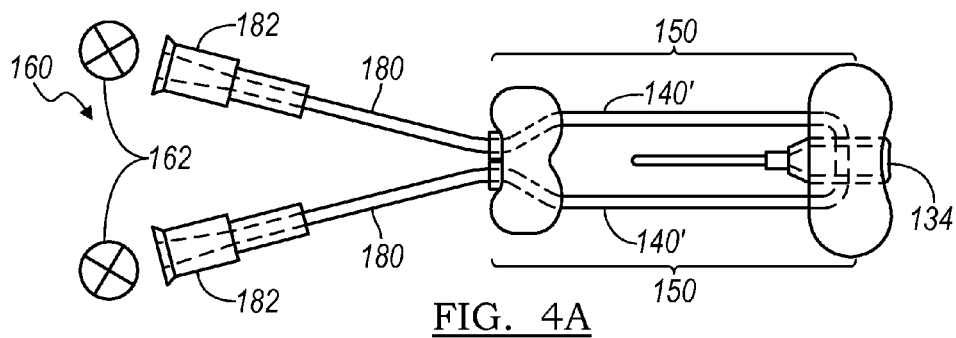
FIGS. 4A-4D are semi-transparent overhead views of variations of the integrated vascular delivery system of another preferred embodiment.
Figure 4B:
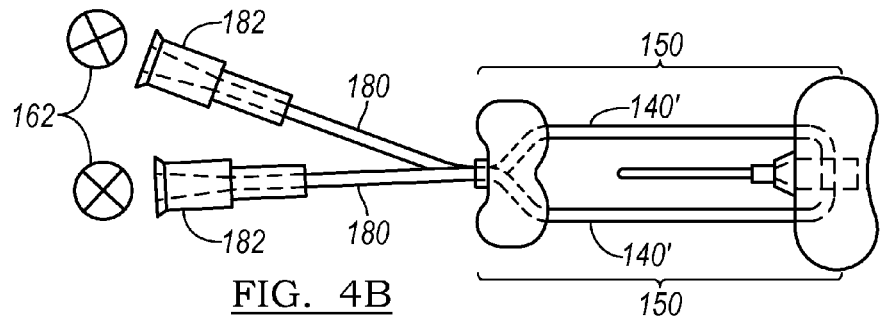
Figure 4C:
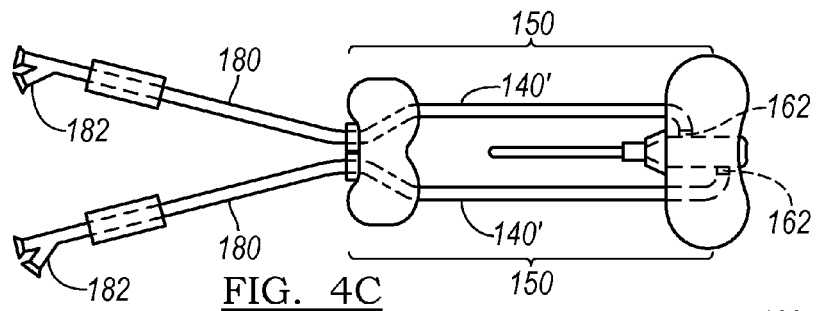
Figure 4D:
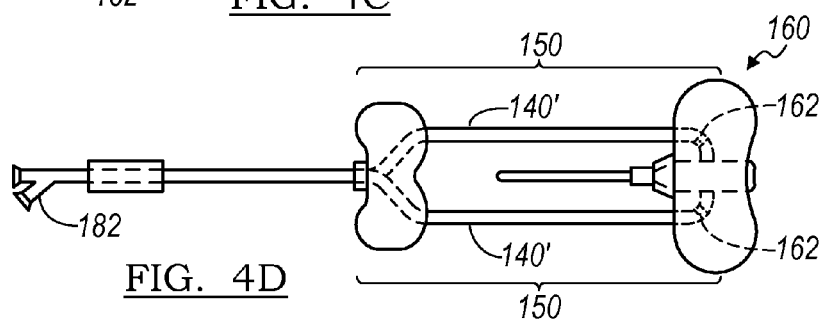

As shown in FIG. 3, in a second preferred embodiment, the pair of lateral members includes two tubular lateral members 140', similar to the tubular lateral member of the first preferred embodiment. In this embodiment, the tubular lateral members 140' are preferably identical and house two separate fluidic channels that direct a first and a second fluid flow between the hubs. However, the tubular lateral members may alternatively be different for serving different purposes. For example, two tubular lateral members 140' may house two separate fluidic channels that are adapted to carry different types of fluids (e.g., different densities), and the tubular lateral members may have different wall thicknesses to compensate for the different fluids and achieve structural symmetry in the frame. As another example, the tubular lateral members may have different sized lumens.

In some alternative versions, the frame 110 may include fewer or more than two lateral members, in any suitable combination and permutation of tubular and solid lateral members. All of the lateral members may be solid, tubular, or hollow, or any combination thereof. In some alternative versions, the lateral members may merge and/or branch upstream and/or downstream. For example, in one alternative embodiment the lateral members may include portions of a thin, flexible sheet that are merged proximal and distal to the insertion site, such that the catheter tip passes through a slot-like opening between the merged portions.

The fluidic channel 150 of the system functions to deliver fluid from a fluid supply to the catheter, and in some embodiments, deliver fluid to and from the catheter. The fluidic channel 150 may additionally and/or alternatively deliver fluid from the catheter 170, such as transferring fluid removed from the patient through the catheter to an external reservoir.

As shown in FIG. 2, the fluidic channel 150 preferably includes at least one portion that is fixed within at least one of the hubs and/or within a tubular lateral member 140'. More preferably, the fluidic channel 150 includes a first portion 152 fixed within the first hub 120, a second portion 154 passing through a tubular lateral member 140', and a turnabout portion 156 fixed within the second hub 130. In a first variation, the fluidic channel 150 may be a continuous length such as a single piece of tubing fixed in the first hub, passing through or serving as the tubular lateral member 140', fixed in the second hub 130 and fluidically coupled to the catheter. In a second variation, the fluidic channel 150 includes separate lengths such as separate tubing segments joined at various points such as through heat sealing, other plastic welding methods, or fluidic couplings. In a third variation, the fluidic channel 150 includes tubular cavities within one or both hubs, to which a tubular segment joins through a process similar to the second variation. In the third variation, the tubular cavities in the first and/or second hub may be formed by molding, drilling, laser cutting, or in any suitable manufacturing process. In a fourth variation, the fluidic channel 150 may be external to one or more of the hubs and lateral members, such that at least a portion of the fluidic channel is mounted to and passes over the exterior of a hub or lateral member. Other variations of the fluidic channel include every combination and permutation of these variations.

As shown in FIG. 2, the first portion 152 of the fluidic channel 150 preferably includes an inlet located at the midline of the proximal side of the first hub and an outlet located on the distal side of the first hub, relative to the midline of the patient. However, the inlet and outlet of the internal channel may be located on any suitable position on the first hub. The inlet of the first portion of the fluidic channel 150 preferably receives fluid from the extension tubing 180, and the outlet of the internal channel preferably delivers the fluid to at least one of the lateral members of the frame 110, but fluid may alternatively flow in reverse order. The first portion of the fluidic channel 150 preferably includes right angles to direct fluid from the midline of the first hub to a tubular lateral member 140' located on the side of the frame. However, the first portion of the fluidic channel may alternatively be curved (shown in FIGS. 3 and 4), curvilinear, or any suitable shape for fluid flow through the first hub 120 to the lateral member. The first portion of the fluidic channel may be connected to the extension tube by inserting the extension tube into a hollow recess aligned with the fluidic channel in the first hub and sealing the recess edge with epoxy, but the first hub may alternatively be coupled to the extension tube by press fitting the extension tube into the recess in the first hub, sealing a butt joint with epoxy, or any suitable coupling process.

As shown in FIG. 2, the second portion 154 of the fluidic channel 150 preferably passes through a tubular lateral segment, between the first portion in the first hub 120 and the turnabout portion in the second hub 130.

As shown in FIG. 2, the turnabout portion 156 of the fluidic channel 150 is preferably fixed in such a way to direct fluid flow in a direction different from fluid flow within the catheter 170. The turnabout portion preferably directs fluid flow to a direction opposite of that within the catheter, or in an approximately 180-degree turn. The turnabout portion 156 may include right angles, an elliptical, or a circular turn. The turnabout portion of the fluidic channel is preferably fixed or embedded within the second hub 130 (distal relative to the midline of the patient). Since the catheter is typically inserted in the patient such that its penetrating end points proximally towards the heart of the patient, the approximate 180-degree turn of fluid flow within the internal channel allows the extension tubing to lie proximal to the insertion site 112 relative to the midline of the patient. This position of the fluid supply channel advantageously allows a stand supporting the IV bag or other fluid supply to be kept near the head of a bed or otherwise proximal to the insertion site relative to the midline of the patient, as is typically desired and practiced in patient treatment settings. The internalized fluid flow turn in the turnabout portion of the fluidic channel 150 also is advantageous because it reduces external features that can get caught or snagged on nearby obstacles and disturb the IV setup. Another effect of the turnabout portion is that if the extension tube and/or additional tubing from a fluid supply is pulled or caught, the turnabout portion may enables the frame to stabilize the catheter more effectively by causing the catheter to be pulled further into the patient. For example, in a common catheter placement where the catheter is placed on the forearm with its distal tip pointing proximally towards the crook of the elbow of the patient, if the extension tubing is accidentally pulled posteriorly towards the patient, the tubing will in turn pull the turnabout portion of the fluidic channel and the distal second hub 130 in a posterior direction, thereby pulling the catheter tip proximally and further into the blood vessel of the patient.

In another preferred embodiment, as shown in FIGS. 3-4, the system includes a second fluidic channel 150 that is preferably similar to the first fluidic channel 150, but may alternatively be any of the variations of the first fluidic channel. The second fluidic channel preferably passes through a second tubular lateral member 140'. The second fluidic channel preferably receives a second fluid, which may be the same or different from the first fluid supplied to the first fluidic channel. In this embodiment, as shown in FIGS. 4A-4C, the system may further include a second extension tube 180 that supplies a second fluid to the second fluidic channel. However, as shown in FIG. 4D, the system may include only one extension tube that supplies fluid to one or both fluidic channels. The fluidic channels may have separate inlets on the first hub or may share the same inlet on the first hub in which flow may be regulated with valves or other fluid control means. In one variation, the first and second fluidic channels preferably fluidically communicate with the same catheter in the second hub 130, coupled to the catheter at the same (FIG. 4D) or different points (FIG. 4C) along the length of the catheter. In this variation, the system preferably includes a flow control system 160 that selectively restricts flow of one or both of the fluids to the catheter and therefore to the patient. The flow control system may include one or more valves 162, such as at the extension tubes (FIGS. 4A-4B), at the junction with the catheter 170 (FIG. 4C-4D), or any suitable location. The flow control system 162 may additionally and/or alternatively use pressure drops, vents, or any suitable technique for controlling fluid flow among the fluidic channels and catheter. The flow control system 162 may also be present in an embodiment that includes only one fluidic channel. In another variation, the first and second fluidic channels preferably fluidically communicate with a catheter with dual lumens, such that one catheter lumen is coupled to the first fluidic channel and another catheter lumen is coupled to a second fluidic channel. In yet another variation, the first and second fluidic channels fluidically communicate with separate catheters. Additional variations expand on these variations with three or more fluidic channels.

Furthermore, the first hub 120 and/or second hub 130 may include multiple internal channels that merge downstream, such that the number of inlets is greater than the number of outlets in the hub. In some variations, one of the hubs may include one or more internal channels that branch downstream, such that the number of inlets is less than the number of outlets. One of the hubs may include one or more internal channels that both branch and merge within the first hub. Multiple internal channels may deliver fluid to multiple catheters or multiple lumens of a catheter.

In some embodiments, the system further includes a catheter 170 having a proximal portion embedded in a portion of the frame, and more preferably in the first or second hub 130. The catheter 170 of the integrated vascular system functions to administer fluids for IV therapy to the patient. The catheter 170 is preferably a conduit insertable into a blood vessel of the patient, but may be any suitable type of catheter. As shown in FIGS. 1-4, the catheter is preferably fluidly connected to the turnabout portion of the fluidic channel and located at the midline of the proximal side of the second hub 130 relative to the midline of the patient. The catheter 170 is preferably aligned with the extension tubing, which reduces and streamlines extraneous external tubing and other connections that may get caught or snagged on nearby obstacles, which is painful and dangerous for the patient. However, the catheter may be positioned at any suitable location on the second hub. In some embodiments, the catheter may be positioned such as having its proximal end fluidically connected to the first, more proximal hub and pointing towards and such that the system lacks a turnabout portion of the fluidic channel. For example, the catheter may be fluidic connected to the first hub that is more proximal to the patient, The catheter is preferably made of a soft, flexible polymer but may be made out of any suitable material. Dimensions of the catheter, including length, diameter, and cannula size, will depend on the specific application. Catheters are known and used in the art, such as that described in U.S. Pat. No. 5,358,493 entitled "Vascular access catheter and methods for manufacture thereof", which is incorporated in its entirety by this reference. The catheter may include markings, such as those similar to a ruler, along its length to indicate the depth to which the catheter is inserted into the patient.

2. Method of Using an Integrated Vascular Delivery System

As shown in FIGS. 5A-5F, the method 200 of an integrated vascular delivery system preferably includes the steps of: supplying a frame forming a perimeter S210, wherein the frame is configured to receive a catheter having a distal end contained within the perimeter and includes a first hub, a second hub, and a fluidic channel; folding the frame to modify the perimeter of the frame S220, thereby freeing the distal end of the catheter from the perimeter of the frame; inserting the catheter into the patient at an insertion site S230; unfolding the frame to restore the perimeter of the frame around the distal end of the catheter and insertion site S240; securing the frame to the patient at a plurality of anchoring points distributed around the insertion site S250, thereby stabilizing the catheter relative to the insertion site; and allowing fluid to flow between the catheter and the patient S260. The method 200 may be performed to obtain access to the blood vessel of a patient, such as one undergoing intravenous (IV) therapy. The method may be used to administer drugs, antibiotics, saline, blood, or any suitable fluid to a patient, and/or to remove fluid from the patient. The method may be used to create, stabilize, and maintain an IV line at an insertion site on a peripheral vein or artery such as on the arm, hand, or leg, or for central venous access on the neck, chest, or abdomen, or any suitable IV location. Furthermore, the method may be used to create, stabilize, and maintain any suitable catheter-based access to a patient, such as catheters for transfer of cerebrospinal fluid.

Figure 5A:
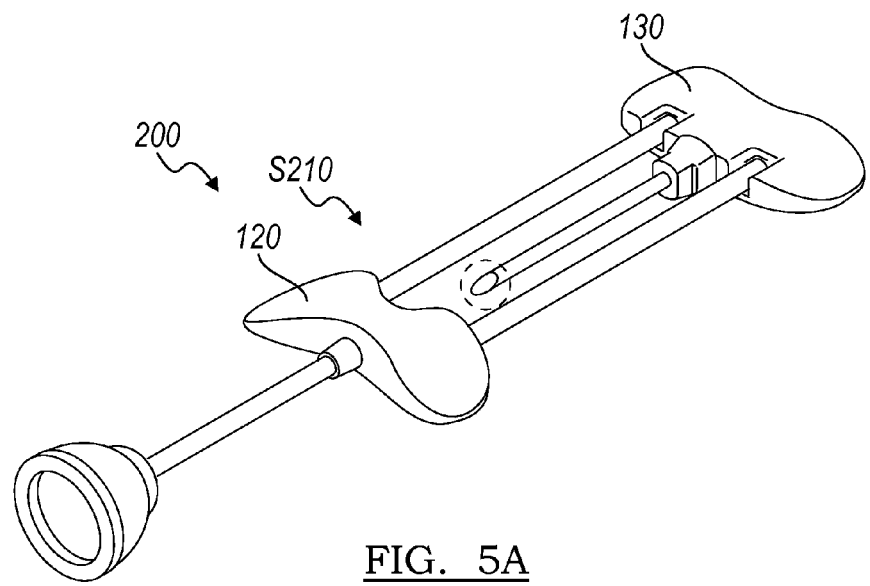
FIGS. 5A-5F are schematics of a method for using the integrated vascular delivery system of a preferred embodiment.
Figure 5B:
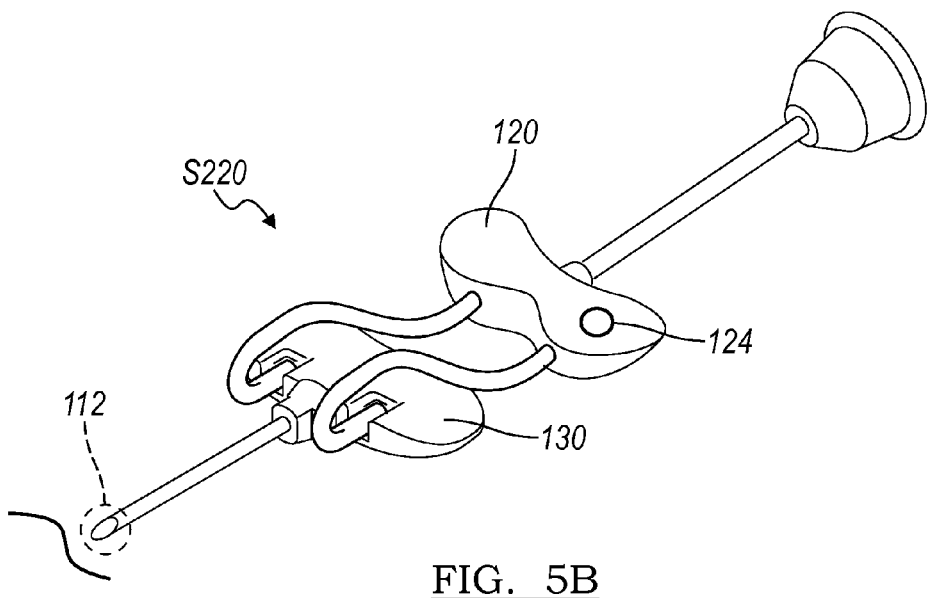

As shown in FIG. 5A, the step of supplying a frame S210 preferably includes supplying an integrated vascular delivery system such as that described above. However, the integrated vascular delivery system may alternatively be any suitable system with a frame, first hub and second hub, and a fluidic channel in which the frame can be folded to pass the first hub towards the second hub. For example, a frame forming a perimeter may include a first hub and a second hub coupled with a hinged joint. Furthermore, the integrated vascular delivery system may include fewer or more hubs.

Figure 5C:
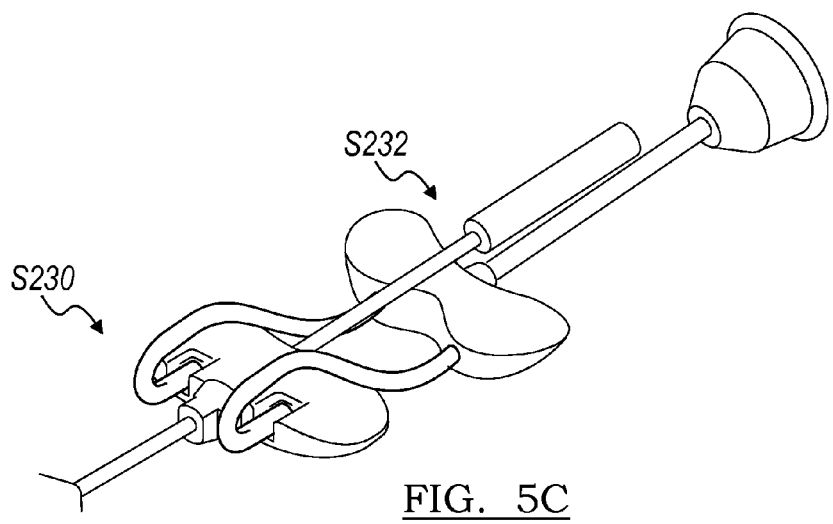
Figure 5D:
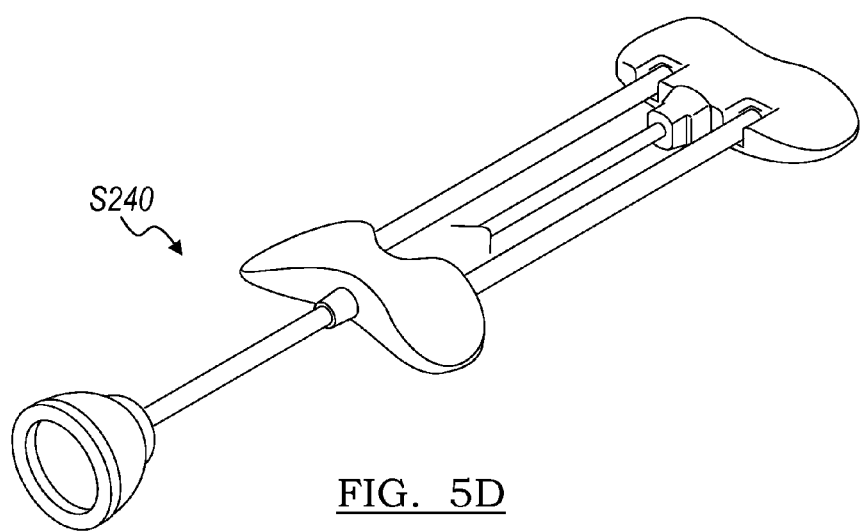
Figure 5E:
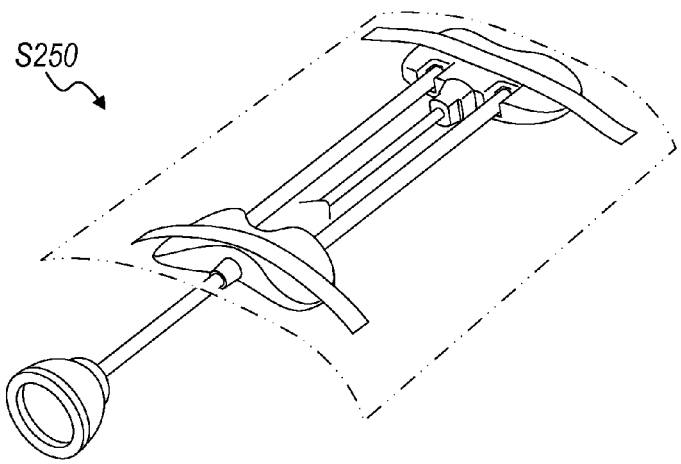
Figure 5F:
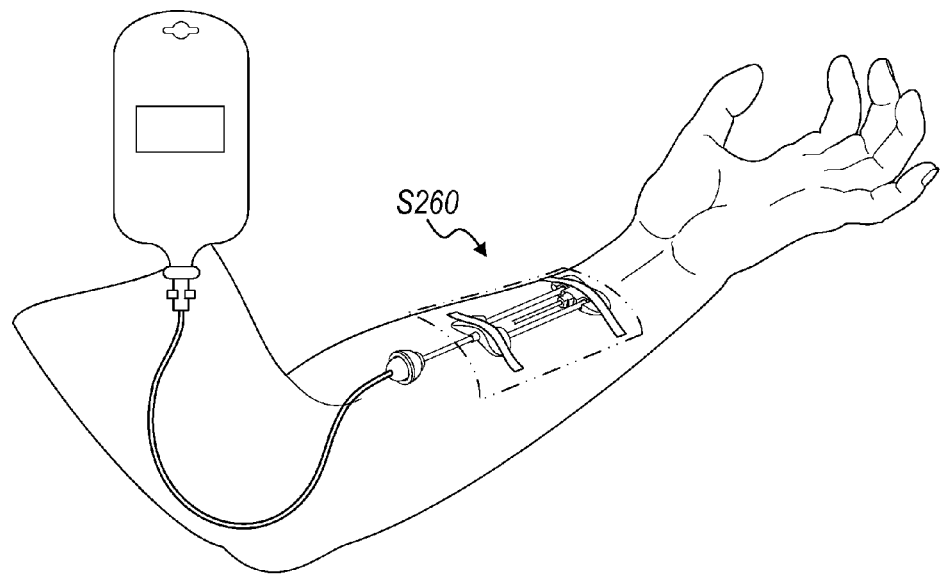
Figure 6A:
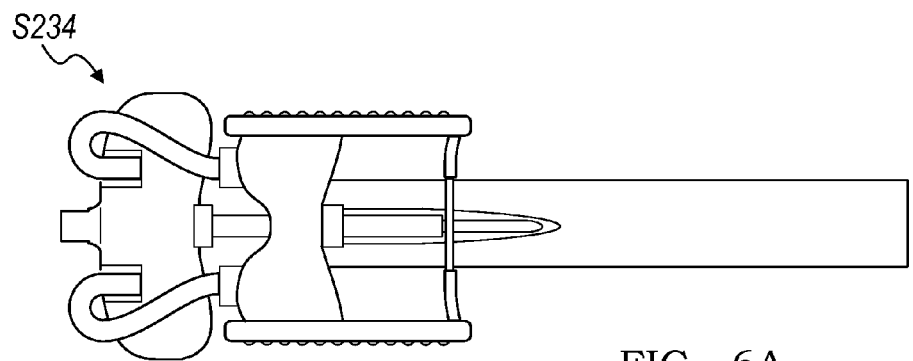
FIGS. 6A-6C are overhead, side, and perspective views, respectively, of a variation of the step of folding in a method for using the integrated vascular delivery system of a preferred embodiment.

The step of folding a frame S220 functions to expose an insertable end of the catheter and to provide visual clearance for the catheter to be positioned at an insertion site and physical clearance to access the insertion site. As shown in FIGS. 5B and 6A, the step of folding the frame preferably includes passing the first hub of the frame over the second hub of the frame in a first direction. The first hub of the frame is preferably a proximal portion of the frame relative to the patient midline, and the second hub of the frame is preferably a distal portion of the frame relative to the patient midline, but the first hub and second hub may be any suitable portions of the frame. For example, as shown in FIG. 5F, relative to an insertion site at the crook of an elbow of a patient, the first hub is preferably closer to the elbow and the second hub is preferably closer to the hand, such that the step of folding a frame folds the first hub away from the patient, and typically towards a medical caregiver using the system who is standing in front of the patient.

Figure 6B:
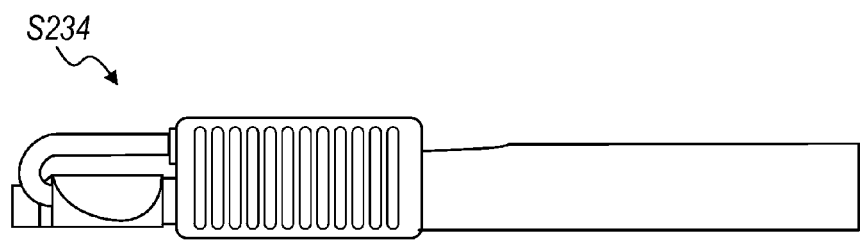
Figure 6C:
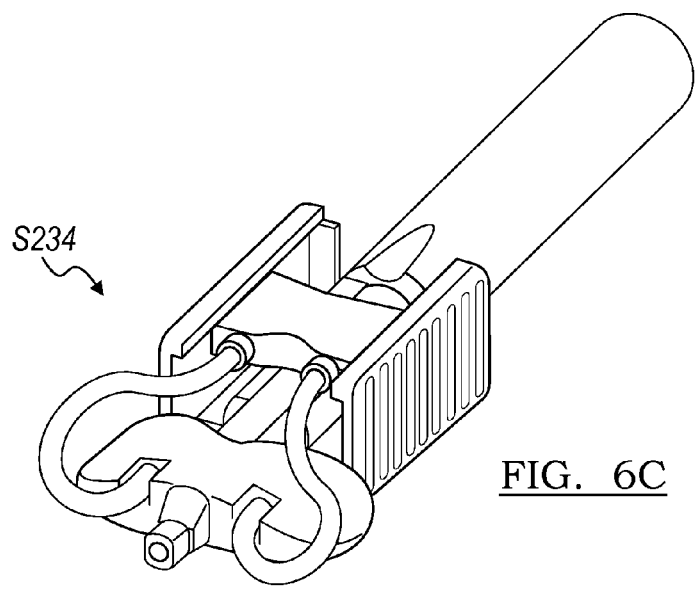

The step of inserting the catheter into the patient at an insertion site S230 includes inserting a needle into a catheter, penetrating the insertion site with the needle, positioning the catheter within the insertion site, and withdrawing the needle from the catheter. The step of inserting the catheter into the patient functions to create a conduit through which fluid can be administered to the patient. In performing the step of penetrating the insertion site with the needle, the needle is preferably pointed proximally relative to the midline of the patient. The step of inserting a needle into a catheter preferably includes inserting a needle through the second hub of the frame, which introduces a piercing tool that is adapted to penetrate the insertion site for catheter insertion. The steps of penetrating the insertion site, positioning the catheter, and withdrawing the needle are known and used by one ordinarily skilled in the art. As shown in FIG. 5C, in a first variation, inserting a needle through the catheter includes passing the needle over the first hub of the frame and through the catheter S232, which maintains the folded orientation of the frame during catheter insertion and to help hold the first hub in place to prevent the first hub from obstructing needle access to the second hub. As shown in FIGS. 6A-6C, in a second variation, inserting a needle through the catheter includes passing the needle under the first hub of the frame and through the catheter S234. In this second variation, the first hub is preferably seated in, or otherwise coupled to an additional mechanism such as a needle housing.

The step of unfolding the frame S240 functions to restore the perimeter of the frame around the distal end of the catheter and insertion site. As shown in FIG. 5D, the step of unfolding the frame preferably includes passing the first hub of the frame over the second hub of the frame in a second direction. The second direction is preferably opposite of the first direction, but may alternatively be any suitable direction and restores the perimeter of the frame around the insertion site. The step of unfolding the frame is facilitated by the step of withdrawing the needle from the catheter, since the needle or other mechanism to which the first hub is coupled is no longer present to hold the first hub in place.

The step of securing the frame to the patient S250 at a plurality of anchoring points around the insertion site functions to stabilize the catheter relative to the insertion site. As shown in FIG. 5E, the step of securing the frame to the patient includes securing the first hub of the frame to the patient at a first anchoring point adjacent to the insertion site, and securing the second hub of the frame to the patient at a second anchoring point opposite the first anchoring point across the insertion site. The plurality of anchoring points preferably include at least two anchoring points approximately opposite to each other, and more preferably include anchoring points distributed approximately equally around the insertion site. In particular, the first anchoring point is preferably distal to the insertion site and the second anchoring point is preferably proximal to the insertion site, relative to the patient. Securing the frame to the patient on two opposite sides of the insertion site functions to effectively reduce or eliminate motions of the catheter within the vein and reduce or eliminate the occurrence of painful and patient-endangering complications including catheter dislodgement, infiltration, and phlebitis. In some variations, the step of securing the frame includes securing any suitable number of hubs at one anchoring point or three or more anchoring points. The first anchoring point is preferably proximal to the insertion site relative to the midline of the patient, and the second anchoring point is preferably distal to the insertion site relative to the midline of the patient, but the first anchoring point and second anchoring point may be at any suitable location relative to the insertion site. Each securing step may include taping the frame to the patient, adhering the frame to the patient with adhesive, strapping the frame to the patient, or any suitable securing mechanism.

The step of allowing the fluid to flow between the catheter and the patient S260 functions to administer fluid to the patient and/or remove fluids from the patient. As shown in FIG. 5F, the step of allowing the fluid to flow preferably includes connecting the fluidic channel to a fluid supply or reservoir. The fluidic channel is preferably connected to the fluid supply or reservoir by fluidly connecting fluidic channel to extension tubing as is well known in the art, but may alternatively be connected to the fluid supply by connecting any suitable portion of the frame through any suitable method. The fluid supply is preferably an IV bag, but may alternatively be any suitable fluid supply. In some variations in which the integrated vascular delivery system includes multiple fluidic channels, the step of allowing the fluid to flow includes connecting a second fluidic channel to a second fluid supply or reservoir.

The method may additionally further include the step of applying a dressing over the insertion site and the frame. The step of applying a dressing functions to protect the insertion site against bacteria, viruses, and other pathogens. The dressing is preferably a breathable, sterile dressing such as Tegaderm, which is known and used to one skilled in the art. As shown in FIG. 5F, the dressing is preferably transparent to allow visualization of the insertion site, and includes adhesive to attach to the skin of the patient and to provide securement of the frame. However, the dressing can include any suitable device or method to assist in the protection of the insertion site.

As a person skilled in the art will recognize from the previous detailed description and from the figures and claims, modifications and changes can be made to the preferred embodiments of the invention without departing from the scope of this invention defined in the following claims.

We Claim:
1. An integrated vascular delivery system adapted to be placed about an insertion site on a patient, comprising:

a frame configured to receive a catheter insertable in the patient to transfer a fluid at the insertion site, wherein the frame includes:
- a first hub that provides a first anchoring point on the patient;
- a second hub that provides a second anchoring point on the patient; and
- a pair of flexible lateral members, including a tubular lateral member defining a lumen, extending between the hubs and configured to be spaced apart from the catheter;
- wherein the first and second anchoring points are configured to be distributed around the insertion site to anchor the frame to the patient, thereby stabilizing the catheter; and a fluidic channel that fluidically communicates with the catheter, wherein the fluidic channel passes through the lumen of the tubular lateral member and at least one of the hubs, and includes a fixed turnabout portion in which fluid flows in a direction different from that within the catheter.

2. The system of claim 1, wherein the system further comprises a catheter, wherein a proximal portion of the catheter is embedded in a portion of the frame, relative to the catheter.

3. The system of claim 2, wherein the proximal portion of the catheter is embedded in the first or second hub.

4. The system of claim 1, wherein the first anchoring point is configured to be distal to the insertion site and the second anchoring point is configured to be proximal to the insertion site, relative to the patient.

5. The system of claim 1, wherein the lateral members are reversibly bendable to fold one of the first and second hubs over the other hub.

6. The system of claim 5, wherein the lateral members are substantially parallel, such that the frame is configured to form an approximately rectangular perimeter around the insertion site.

7. The system of claim 1, wherein the turnabout portion of the fluidic channel is fixed within one of the hubs.

8. The system of claim 7, wherein the turnabout portion of the fluidic channel directs fluid flow in a direction opposite of fluid flow within the catheter.

9. The system of claim 1, wherein at least one of the hubs includes a sensor that measures a biometric or fluid parameter.

10. The system of claim 1, wherein the pair of lateral members includes a solid lateral member.

11. The system of claim 1, wherein the lateral members include a second tubular member, wherein the system further comprises a second fluidic channel that fluidically communicates with the catheter and passes through the second tubular member and at least one of the hubs.

12. The system of claim 11, wherein the second fluidic channel receives a second fluid.

13. The system of claim 12, wherein the second fluidic channel receives a second fluid that is different from the first fluid.

14. The system of claim 12, wherein the system comprises a first extension tube that delivers a first fluid to the first fluidic channel, and a second extension tube coupled to the second fluidic channel that delivers a second fluid to the second fluidic channel.

15. The system of claim 11, wherein the catheter is a dual lumen catheter including a first lumen coupled to the first fluidic channel and a second lumen coupled to the second fluidic channel.

16. The system of claim 1, further comprising a flow control system that selectively restricts flow of the fluid through the catheter.

17. The system of claim 16, wherein the flow control system includes at least one valve.

18. An integrated vascular delivery system adapted to be placed on a patient, comprising:
- a catheter having a proximal end that receives fluid and a distal end that delivers the fluid to the patient at an insertion site;
- a frame that provides an approximately rectangular perimeter surrounding the insertion site, including:
  - a first hub that provides a first anchoring point on the patient;
  - a second hub that provides a second anchoring point on the patient;
  - a pair of flexible lateral members, including a tubular lateral member defining a lumen, extending between the hubs and spaced apart from the catheter on opposite sides of the catheter;
  - wherein the first and second anchoring points are on opposite sides of the insertion site to anchor the frame to the patient, thereby stabilizing the catheter;
  - wherein the lateral members are reversibly bendable to fold one of the first and second hubs over the other hub; and
- a fluidic channel that fluidically communicates with the catheter, wherein the fluidic channel passes through the lumen of the tubular lateral member and at least one of the hubs, and includes a fixed turnabout portion in which fluid flows in a direction opposite from that within the catheter.

19. The system of claim 18, wherein the pair of lateral members includes a solid lateral member.

20. The system of claim 18, wherein the lateral members include a second tubular member, wherein the system further comprises a second fluidic channel that fluidically communicates with the catheter and passes through the second tubular member and at least one of the hubs.

21. A method of using an integrated vascular delivery system, comprising:
- supplying a frame forming a perimeter, wherein the frame includes: a first hub, a second hub, a catheter comprising a distal end contained within the perimeter and a proximal end coupled to one of the first and second hubs, at least one flexible lateral member defining a lumen and extending between the first and second hubs, and a fluidic channel that fluidically communicates with the catheter and passes through the lumen of the lateral member and at least one of the first and second hubs;
- folding the frame to modify the perimeter of the frame, thereby freeing the distal end of the catheter from the perimeter of the frame;
- inserting the catheter into the patient at an insertion site;
- unfolding the frame to restore the perimeter of the frame around the distal end of the catheter and insertion site;
- securing the frame to the patient at a plurality of anchoring points distributed around the insertion site, thereby stabilizing the catheter relative to the insertion site; and
- allowing fluid to flow between the catheter and the patient.

22. The method of claim 21, wherein folding the frame includes bending the lateral member to pass the first hub over the second hub.

23. The method of claim 22, wherein inserting the catheter includes passing a needle over the first hub and through the catheter.

24. The method of claim 22, wherein inserting the catheter includes passing a needle under the first hub and through the catheter.

25. The method of claim 21, wherein securing the frame includes securing the first hub at a first anchoring point distal to the insertion site and securing the second hub at a second anchoring point proximal to the insertion site.

* * * * *